United States Patent
Nichols et al.

[11] Patent Number: 6,145,687
[45] Date of Patent: *Nov. 14, 2000

[54] CONTAMINANT PLUG FOR MEDICAL INSTRUMENT STERILIZATION CONTAINERS

[75] Inventors: Robert L. Nichols; William H. Patterson, both of Jacksonville; Keith F. Lindsey, Troup, all of Tex.

[73] Assignee: Johnson & Johnson Medical, Inc., New Brunswick, N.J.

[*] Notice: This patent is subject to a terminal disclaimer.

[21] Appl. No.: 09/338,162

[22] Filed: Jun. 22, 1999

Related U.S. Application Data

[60] Continuation of application No. 08/455,201, May 31, 1995, Pat. No. 5,954,219, which is a division of application No. 08/140,215, Oct. 21, 1993, Pat. No. 5,474,738, which is a continuation of application No. 07/664,352, Mar. 4, 1991, Pat. No. 5,324,489.

[51] Int. Cl.$^7$ ........................................... A61L 2/00
[52] U.S. Cl. ........................ 220/256; 220/361; 220/370; 220/371; 422/292
[58] Field of Search .................... 220/256, 300, 220/361, 370, 371, 360, 367.1; 422/292, 310, 297, 300; 206/363

[56] References Cited

U.S. PATENT DOCUMENTS

| | | | |
|---|---|---|---|
| 2,342,067 | 2/1944 | Turner | 422/300 |
| 2,727,650 | 12/1955 | Moynihan et al. | 220/230 |
| 2,784,843 | 3/1957 | Braunlich | 210/247 |
| 2,959,832 | 11/1960 | Baermann | 24/303 |
| 2,962,185 | 11/1960 | Starr et al. | 220/254 |
| 3,124,725 | 3/1964 | Leguillon | 335/303 |
| 3,410,395 | 11/1968 | Sellers | 206/439 |
| 3,437,423 | 4/1969 | Mondiadis | 206/511 |
| 3,454,189 | 7/1969 | Lauterbach | 206/216 |
| 3,480,145 | 11/1969 | Gladden | 210/223 |
| 3,697,223 | 10/1972 | Kovalcik et al. | 206/370 |
| 3,750,827 | 8/1973 | Wick | 220/619 |

(List continued on next page.)

FOREIGN PATENT DOCUMENTS

| | | |
|---|---|---|
| 152544 | 11/1984 | European Pat. Off. |
| 2542200 | 9/1984 | France . |
| 2165754 | 4/1986 | United Kingdom . |

*Primary Examiner*—Joseph M. Moy
*Attorney, Agent, or Firm*—Baker Botts L.L.P.

[57] ABSTRACT

A medical instrument sterilization container (10) is provided which includes a port (18). A removable filter (32) is received within port (18) to enable sterilization of instruments placed within container (10). A removable plug (48) replaces filter (32) to enable container (10) to be used to transport instruments without leaking of fluids therefrom.

11 Claims, 4 Drawing Sheets

U.S. PATENT DOCUMENTS

| | | | |
|---|---|---|---|
| 3,831,759 | 8/1974 | Gelman et al. | 210/232 |
| 3,890,096 | 6/1975 | Nichol et al. | 206/369 |
| 3,946,872 | 3/1976 | Sturm | 220/359 |
| 4,105,407 | 8/1978 | Sanderson | 422/26 |
| 4,121,714 | 10/1978 | Daly et al. | 206/363 |
| 4,124,141 | 11/1978 | Armentrout et al. | 220/306 |
| 4,154,342 | 5/1979 | Wallace | 206/439 |
| 4,196,166 | 4/1980 | Sanderson et al. | 422/300 |
| 4,210,674 | 7/1980 | Mitchell | 426/107 |
| 4,251,482 | 2/1981 | Sanderson et al. | 422/26 |
| 4,267,420 | 5/1981 | Brastad | 219/730 |
| 4,271,973 | 6/1981 | Quagliaro et al. | 215/308 |
| 4,331,067 | 5/1982 | Mysicka et al. | 97/305 |
| 4,359,495 | 11/1982 | Schroeder et al. | 428/458 |
| 4,372,921 | 2/1983 | Sanderson et al. | 422/300 |
| 4,396,583 | 8/1983 | LeBoeuf | 422/301 |
| 4,402,407 | 9/1983 | Maly | 422/300 |
| 4,416,417 | 11/1983 | Sanderson et al. | 236/92 R |
| 4,416,906 | 11/1983 | Watkins | 426/107 |
| 4,457,327 | 7/1984 | Pepper | 422/112 |
| 4,458,705 | 7/1984 | Cawood | 134/135 |
| 4,468,321 | 8/1984 | St. John | 210/232 |
| 4,512,498 | 4/1985 | Leibinger | 220/371 |
| 4,551,311 | 11/1985 | Lorenz | 422/300 |
| 4,584,182 | 4/1986 | Sanderson et al. | 422/310 |
| 4,617,178 | 10/1986 | Nichols | 422/310 |
| 4,704,254 | 11/1987 | Nichols | 422/28 |
| 4,716,025 | 12/1987 | Nichols | 422/310 |
| 4,732,187 | 3/1988 | Monch | 422/297 |
| 4,748,003 | 5/1988 | Riley | 422/112 |
| 4,752,453 | 6/1988 | Nichols et al. | 422/300 |
| 4,783,321 | 11/1988 | Spence | 422/300 |
| 4,859,348 | 8/1989 | Jusaitis et al. | 210/799 |
| 4,860,645 | 8/1989 | van der Lijn et al. | 99/295 |
| 4,900,519 | 2/1990 | Nichols | 422/292 |
| 4,915,918 | 4/1990 | Nichols | 422/292 |
| 5,028,328 | 7/1991 | Long | 210/477 |
| 5,080,874 | 1/1992 | Nichols | 422/300 |
| 5,324,489 | 6/1994 | Nichols et al. | 422/300 |

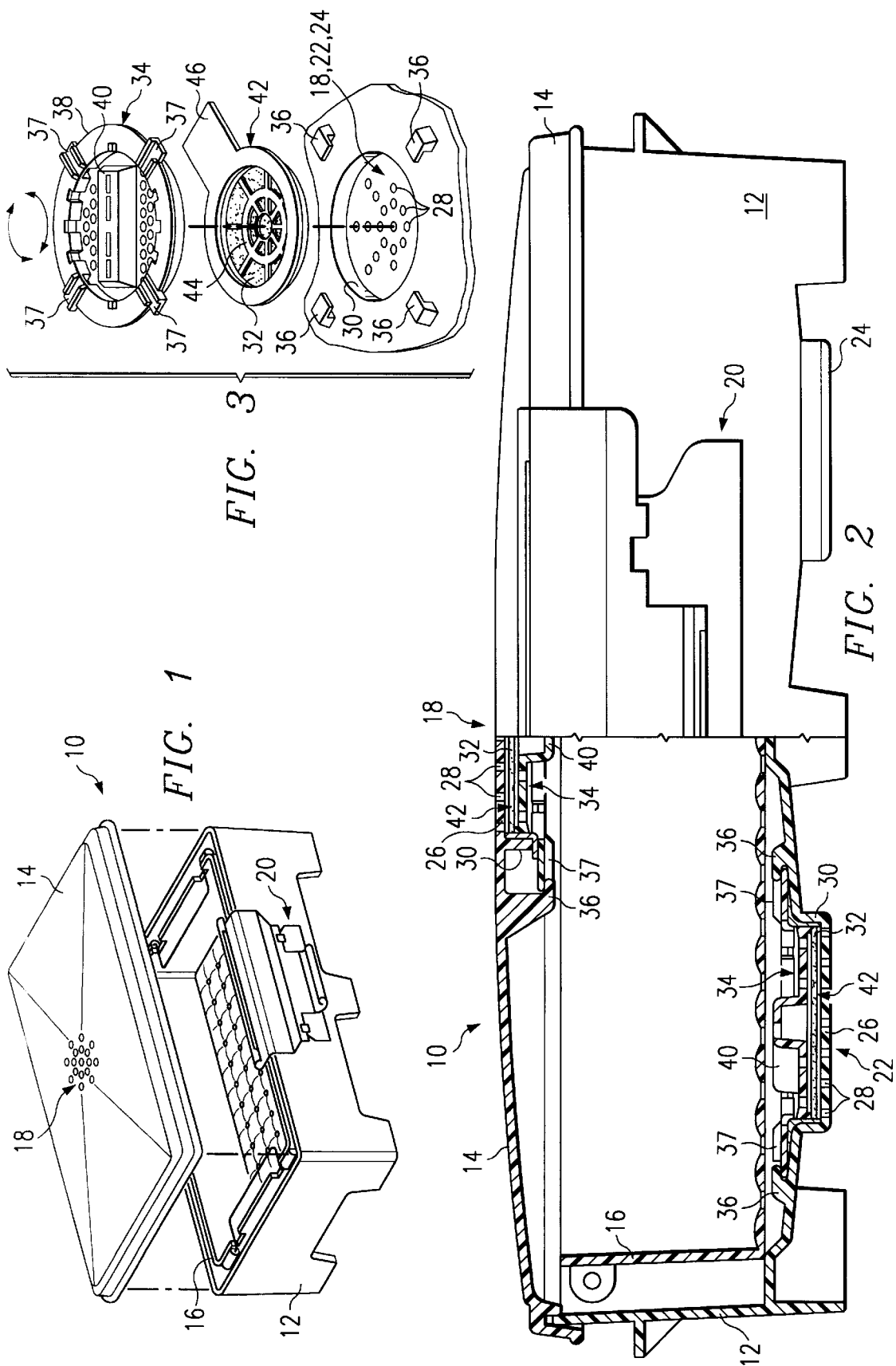

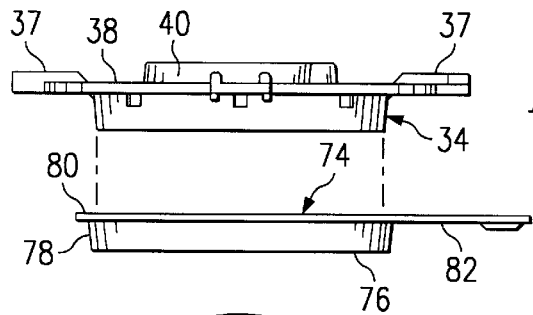
FIG. 6a
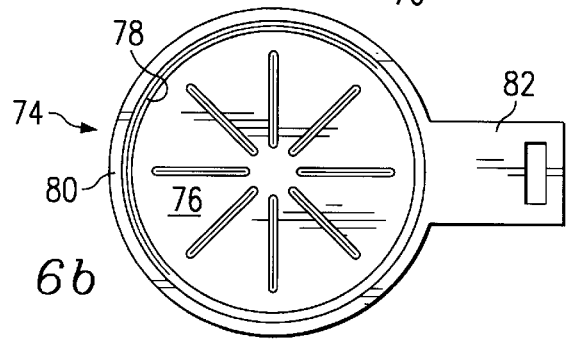
FIG. 6b
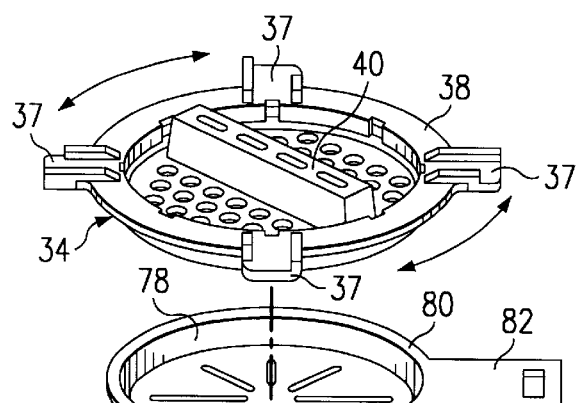
FIG. 6c
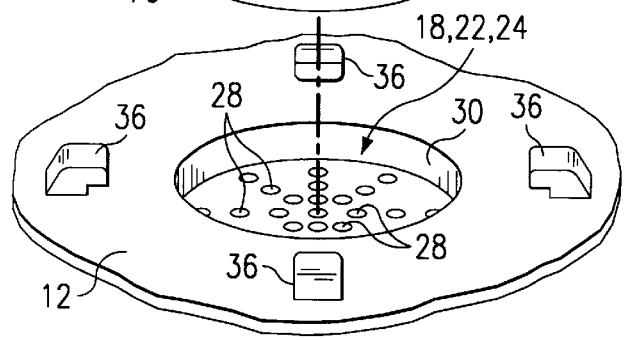
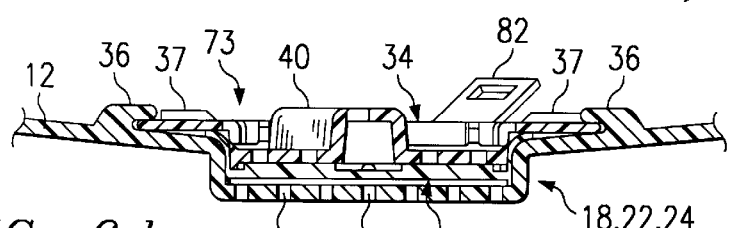
FIG. 6d

CONTAMINANT PLUG FOR MEDICAL INSTRUMENT STERILIZATION CONTAINERS

CROSS-REFERENCE TO RELATED APPLICATIONS

This application is a continuation of U.S. application Ser. No. 08/455,201, filed May 31, 1995, now U.S. Pat. No. 5,954,219 and entitled "Contaminant Plug for Medical Instrument Sterilization Containers" by Robert L. Nichols, William H. Patterson and Keith F. Lindsey, now pending; which is a divisional of U.S. application Ser. No. 08/140,215, filed Oct. 21, 1993, and entitled "Contaminant Plug for Medical Instrument Sterilization Containers" by Robert L. Nichols, William H. Patterson and Keith F. Lindsey, now U.S. Pat. No. 5,474,738, issued Dec. 12, 1995; which is a continuation of U.S. application Ser. No. 07/664,352, filed Mar. 4, 1991, and entitled "Contaminant Plug for Medical Instrument Sterilization Containers" by Robert L. Nichols, William H. Patterson and Keith F. Lindsey, now U.S. Pat. No. 5,324,489, issued Jun. 28, 1994.

TECHNICAL FIELD OF THE INVENTION

The present invention relates generally to the field of medical instrument sterilization containers, and more particularly to a contaminant plug for medical instrument sterilization containers.

BACKGROUND OF THE INVENTION

It is common practice in hospitals and other medical environments to sterilize medical instruments with steam or other sterilizing gases such as ethylene oxide (ETO). Sterilization containers provide a convenient enclosure in which the sterilization can be performed. Additionally, sterilization containers can be used as a storage and containment device for moving contaminated instruments from one location to another, while reducing the probability of cross-contaminating the surrounding environment. Finally, during the transfer of contaminated instruments after surgery, sterilization containers can also be used for soaking medical instruments to prevent blood and other contaminants from drying on the instruments.

Sterilization containers normally have bottom housings with a bottom and sidewalls, removable lids, ports for the passage of sterilization gases and filter means for preventing and inhibiting contaminants from entering the container after sterilization. Containers generally have one or two ports in the lid and one or two ports in the bottom. Both top and bottom ports are needed if the container is to be used for gravity steam or ethylene oxide gas sterilization. In gravity steam processes, steam gases enter the top of the sterilizing container and push air down and out. The lower port is therefore required for air and steam to exit the container. When utilizing ethylene oxide gas sterilization, both top and bottom ports are required during the aeration process in which air is passed through a container to remove residual ethylene oxide gas remaining after sterilization.

The need for both top and bottom ports in the gravity steam and ethylene oxide processes reduces the utility of the sterilization container for soaking and transportation applications. If the container is to be utilized as a receptacle for soaking instruments after surgery, or for transporting contaminated instruments, the bottom or outlet ports will create problems. It has been recognized in the medical industry that filtered or open ports in the sterilization container bottom may allow soaking fluids or contaminants to leak or pass through to the outside, thereby contaminating the surroundings. This is even often true with hydrophobic type filters which are generally perceived to pass only gases and not liquids or solids. Even with such hydrophobic type filters, there is still the concern that small amounts of contaminants may seep through the filter or around the seal.

The need has therefore arisen for a plug which can seal a container port such that contaminants, whether liquid or solid, cannot escape. Such a plug would allow the use of a medical instrument sterilization container with both top and bottom ports to be used for the transportation of contaminated medical instruments without the fear of contamination of the surroundings. Further, such a plug would allow a medical instrument sterilization container having a bottom port to be used for soaking medical instruments after surgery without leakage.

SUMMARY OF THE INVENTION

According to the invention, a medical instrument sterilization container is provided which includes a port. A removable filter is provided within the port to enable sterilization of instruments placed within the container. A removable plug is provided which replaces or fits above or below the filter to enable the container to be used to transport instruments placed within the container without permitting the passage of contaminants out of the container.

The present invention provides the advantage of sealing a port on a medical instrument sterilization container such that liquid or solid contaminants cannot escape into the surrounding environment. The medical instrument sterilization container can thus be used as a safe means of transporting contaminated medical instruments without cross contamination between the exterior and interior of the container. Further, by sealing a medical instrument sterilization container according to the present invention, the medical instrument sterilization container can be used as a soaking container for soaking instruments following their use.

BRIEF DESCRIPTION OF THE DRAWINGS

Other aspects of the invention and their advantages will be discerned when one refers to the following detailed description as taken in conjunction with the drawings, in which like numbers identify like parts, and in which:

FIG. 1 is a perspective view of a medical instrument sterilization container;

FIG. 2 is a partial section view of the sterilization container of FIG. 1;

FIG. 3 is an exploded view of a selected port of the medical instrument sterilization container of FIG. 1 and the associated filter and retaining cap;

FIGS. 6a and 6b are respectively top and side views of a contaminant plug according to a third preferred embodiment; and FIGS. 6c and 6d are respectively exploded perspective and cross-sectional views depicting the contaminant plug of a third preferred embodiment engaging a selected port of the medical instrument sterilization container of FIG. 1.

DETAILED DESCRIPTION OF THE INVENTION

Figure 4A:
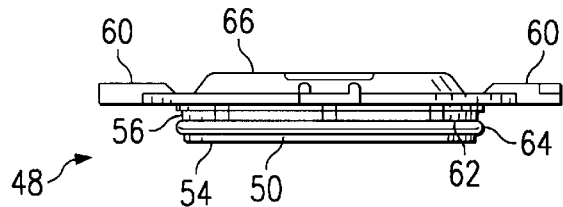
FIGS. 4a and 4b are top and side views of a contaminant plug according to a first preferred embodiment.

Preferred embodiments of the present invention are best understood by referring to FIGS. 1–6 of the drawings, like numerals being used for like and corresponding parts of the various drawings.

Referring first to FIG. 1, a medical instrument sterilization container is shown generally at 10, and includes the housing 12 and a removable lid 14. Lid 14 is preferably domed-shaped as shown in FIG. 1; however, lid 14 may also have other configurations as known in the art, such as being substantially flat. Removable tray 16 is received within the housing 12 and is adapted to receive various medical instruments, such as knives, scissors and the like.

An inlet port 18 is disposed through lid 14 in order to allow the passage of sterilizing steam and gases therethrough, while inhibiting or preventing the passage of dirt, dust, bacteria and other contaminants into the interior of the container. Two outlet ports, to be discussed below, are disposed in the bottom of housing 12. Metal clamps 20 are attached to both sides of the housing 12 and are manually movable to clamp against the side of the lid 14 in order to lock lid 14 to the housing 12. Suitable sealing surfaces are provided between the housing 12 and the lid 14 providing an essentially sealed container when the lid 14 is clamped to housing 12.

FIG. 2 is a partially sectioned view of container 10, which depicts outlet ports 22 and 24 extending from the bottom 25 of housing 12. Ports 18, 22 and 24 each include a circular base plate 26 having a plurality of apertures 28 which communicate with the surrounding atmosphere. In inlet port 18, base plate 26 is an integral part of domed shaped lid 14. Annular sidewalls 30 form a receptacle which is adapted to receive a removable filter 32. Removable filter 32 is held tightly within annular sidewalls 30 by a twistable cover 34 which engages a plurality of locking members 36 disposed around the periphery of the respective port.

Referring next to FIG. 3, an exploded view is shown which demonstrates the cooperation between a selected port 18, 22 or 24 with an associated filter 32 and twistable cover 34. Twistable cover 34 includes four locking flanges 37 which extend from a lip member 38. Locking flanges 37 are positioned to be rotated into locking members 36 formed around the periphery of the respective ports 18, 22 or 24. A gripping member or handle 40 is provided on twistable cap 34 to facilitate its rotation within the respective annular sidewalls 30. A typical filter is shown which is circular in shape and includes a plastic member having a lip 42, plastic cross members 44 and a tab 46 extending from lip 42 to allow manual insertion or removal from the ports 18, 22 or 24.

Figure 4B:
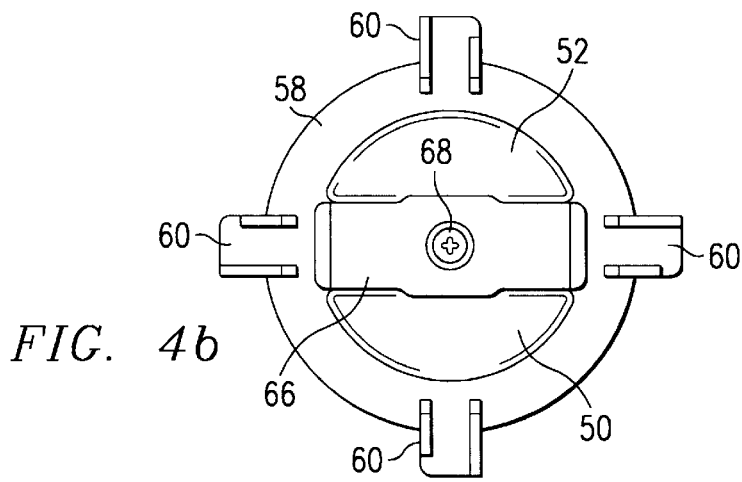

Referring next to FIGS. 4a–b, which are top and side views of a first preferred embodiment, a contaminant plug 48 is designed to seal a selected port 18, 22 or 24. Plug 48 includes a disk-shape cover plate 50 having an upper surface 52, a lower surface 54 and a sidewall 56. Contaminant plug 48 may be made of plastic, metal or any other suitable material. An annular flange 58 extends beyond the periphery of sidewall 56 and includes four locking flanges 60 which are positioned to engage locking members 36 disposed around a selected port 18, 22 or 24. A slot 62 is formed in sidewall 56 around the periphery of cover plate 50. An O-ring seal 64, formed of silicone or another suitable compressible material which is contaminant impermeable, is disposed in slot 62. A gripping member 66 is fastened to cover plate 50 by a screw 68.

Figure 4C:
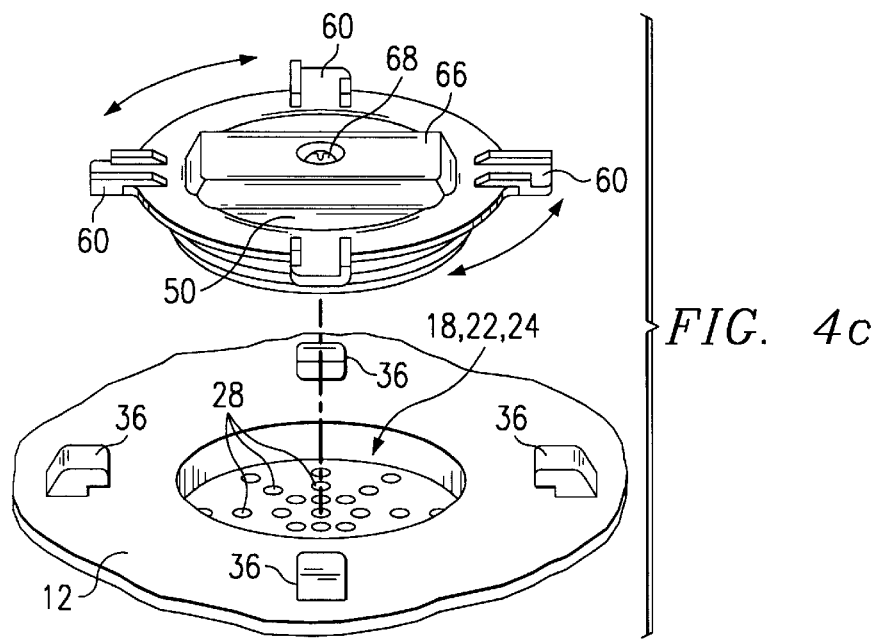
FIGS. 4c and 4d are respectively exploded and cross-sectional views showing the engagement of the contaminant plug of a first preferred embodiment engaging with a selected port of the medical instrument sterilization container of FIG. 1.
Figure 4D:
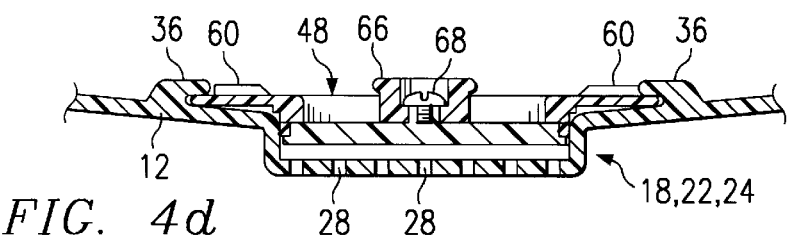

FIGS. 4c and 4d illustrate in detail the engagement of contaminant plug 48 with a selected one of ports 18, 22 or 24. While in the preferred embodiment contaminant plug 48 is shown to be removable, it should be understood by persons skilled in the art that removability is not an essential requirement. FIG. 4c is an exploded perspective view of plug 48 and the selected port prior to engagement. FIG. 4d is a cross-sectional view showing contaminant plug 48 inserted into the selected port 18, 22 or 24 and engaged. Contaminant plug 48 is inserted into the selected port such that O-ring seal 64 is pressed firmly against annular sidewalls of ports 18, 22 and 24. Using gripping member 66, contaminant plug 48 can be twisted within sidewalls 30 such that locking flanges 60 engage locking members 36. Locking flanges 60 are tightly held by locking members 36 such that O-ring seal 64 prevents the passage of contaminants from the interior of housing 12 through apertures 28 of the selected ports 18, 22, or 24.

Contaminant plug 48 may be used by medical personnel in place of filter 32 and twistable cover 34, thus allowing medical instrument sterilization container 10 to be used as a receptacle for soaking instruments following surgery or for transporting medical instruments without cross contamination with the outside environment. When desired, plugs 48 may be removed or opened, thus allowing the container 10 again to be used in connection with the sterilization of medical instruments.

Figure 5A:
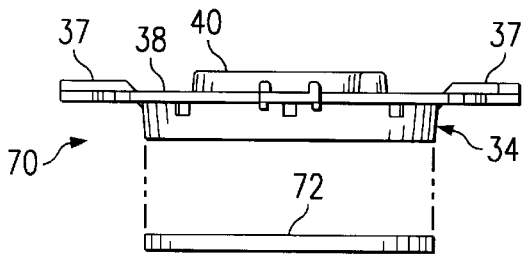
FIGS. 5a and 5b are respectively top and side views of a contaminant plug according to a second preferred embodiment.
Figure 5B:
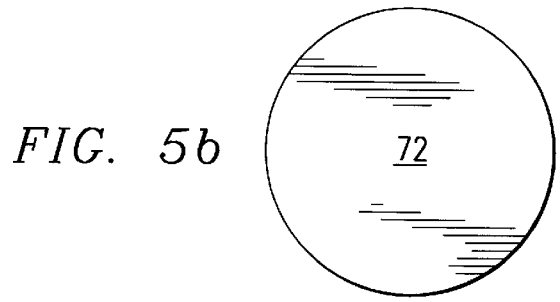
Figure 5C:
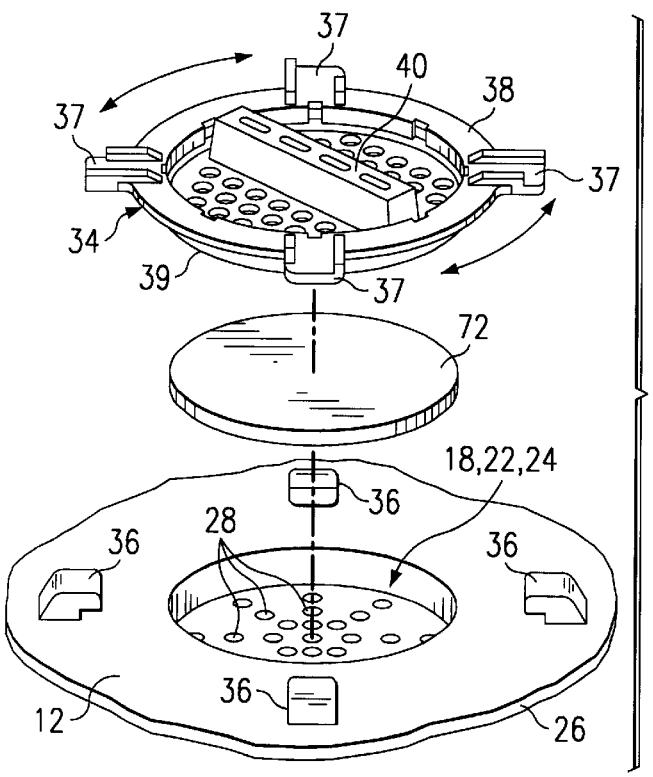
FIGS. 5c and 5d are respectively exploded and cross-sectional views depicting the contaminant plug of a second preferred embodiment engaging a selected port in the medical instrument sterilization container of FIG. 1.
Figure 5D:
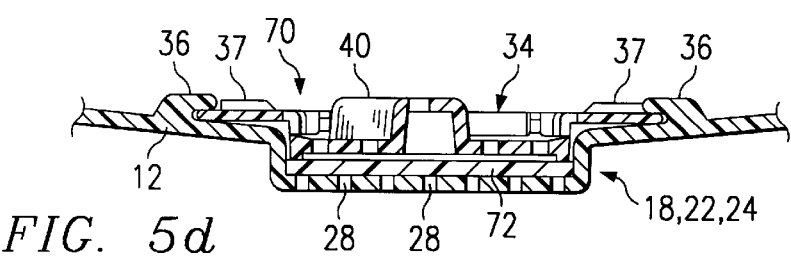

FIGS. 5a and 5b illustrate top and side views of a second embodiment of the present invention. A contaminant plug is shown generally at 70, and includes a twistable cover 34 and a disk-shaped compression seal 72 comprised of silicone or another suitable compressible material. Compression seal 72 is shown as a discrete member inserted directly into a selected port 18, 22 or 24; however, compression seal 72 may be directly fastened to twistable cover 34 to provide a single unit. In either case, compression seal 72 is pressed tightly against the base 26 of the selected port 18, 22 or 24, thereby sealing off perforations 28. The engagement of compression seal 72 and twistable cover 34 is depicted in FIG. 5c which is an exploded perspective view of contaminant plug 70 and a selected port 18, 22 or 24, and FIG. 5d which is a cross-sectional view showing compression seal 72 and cover 34 engaged in the selected port. Contaminant plug 70 has the significant advantage of utilizing the twistable cover 34 already available for retaining filters 32. Further, compression seal 72 may be disposable for convenience.

Turn next to FIGS. 6a and 6b, wherein respective side and top views of a sealing disk 74 are shown for use in a third embodiment contaminant plug. Sealing disk 74 includes a circular base plate 76, an annular sidewall 78 formed at an angle to base plate 76, and a lip member 80 disposed around the edge of annular sidewall 78. Preferably, a tab 82 is fastened to annular sidewall 78 to aid in the insertion and removal of sealing disk 74 from a selected port 18, 22 or 24. Sealing disk 74 may be formed of a plastic or other suitable material that prevents passage of contaminants whether solid, liquid or gaseous.

FIGS. 6c and 6d are respective exploded perspective and cross-sectional views showing the engagement of disk 74 and twistable cover 34 in a selected port 18, 22, or 24. Sealing disk 74 is adapted to be inserted within sidewalls 30 of the selected port. Lip member 80 can seat on the bottom of housing 12 around the immediate periphery of the selected port 18, 22 or 24. A twistable cover 34 then seats within the annular sidewall 78 of sealing disk 74. When twistable cover 34 is twisted such that its locking flanges 37 engage with locking members 36 of the selected port 18, 22 or 24, sealing disk 74 is firmly retained providing the requisite seal. This can be most easily seen by referring to FIG. 6c, which is a perspective view showing a sealing disk 74 and an associated twistable cap 34 inserted and engaged in a selected port 18, 22 or 24. Sealing disk 74, when properly engaged with the selected port 18, 22 or 24, thereby prevents the communication of contaminants between the interior and exterior of medical instrument sterilization container 10.

Thus, the present invention enables a medical instrument sterilization container having inlet and outlet ports to be sealed to prevent the undesired escape of contaminants into the surrounding area. The present invention allows such a medical instrument sterilization container to be used for the safe transport of contaminated medical instruments without the risk of exposing the outside environment. Further, the present invention allows a medical instrument sterilization container to be used as a convenient receptacle for soaking medical instruments following such medical procedures as surgery.

While preferred embodiments of the invention and their advantages have been set forth in the above-detailed description, the invention is not limited thereto, but only by the scope and spirit of the appended claims.

What is claimed is:

1. A method of using a medical instrument and containing associated contaminants, comprising:

inserting the medical instrument into a medical instrument sterilization container, the container comprising a housing, a port defined through the housing and including a perforated base, a locking mechanism disposed about a periphery of the port, a removable filter disposed within the port adjacent the perforated base, and a removable cover disposed adjacent the port and cooperating with the locking mechanism to lock the filter into engagement with the perforated base, removing the medical instrument from the container, unlocking the removable cover, removing the filter from the port, inserting a removable sealing member in the port, replacing the removable cover to lock the sealing member into engagement with the port, and reinserting the medical instrument into the container.

2. The method of claim 1, wherein the step of inserting a removable sealing member comprises attaching the removable sealing member to the cover.

3. The method of claim 2, wherein the step of replacing the removable cover comprises locking the sealing member into engagement with an annular sidewall of the port.

4. The method of claim 3, wherein when the sealing member is locked into engagement, the sealing member is disposed between the annular sidewall of the port and a peripheral sidewall of the cover.

5. The method of claim 1, wherein the step of inverting a removable sealing member comprises inserting a disk of compressible material adapted to insertably engage the port.

6. The method of claim 1, wherein the step of replacing the removable cover comprises locking the sealing member into engagement with the port.

7. The method of claim 1, wherein the step of replacing the removable cover comprises locking the sealing member into engagement with the perforated base.

8. The method of claim 1, wherein when the sealing member is locked into engagement, the sealing member is disposed between the cover and the perforated base.

9. The method of claim 1, wherein when the sealing member is locked into engagement, the sealing member is partially disposed between the cover and the perforated base and partially disposed between an annular sidewall of the port and a peripheral sidewall of the cover.

10. The method of claim 1, wherein the step of inserting a removable sealing member comprises inserting a sealing disk comprising a base and an annular sidewall extending from the base, the base being adjacent a lower surface of the cover and the annular sidewall being adjacent a peripheral sidewall of the cover.

11. The method of claim 10, wherein the sealing disk further comprises a gripping member extending from the annular sidewall of the sealing disk.

* * * * *